(12) United States Patent
Yang et al.

(10) Patent No.: US 10,166,264 B2
(45) Date of Patent: Jan. 1, 2019

(54) BACTERIOPHAGE AND ANTIBACTERIAL COMPOSITION COMPRISING THE SAME

(71) Applicant: CJ CHEILJEDANG CORPORATION, Seoul (KR)

(72) Inventors: Si Yong Yang, Incheon (KR); Jae Won Kim, Seoul (KR); Young Wook Cho, Seoul (KR); Young Sa Kim, Seoul (KR); Eun Mi Shin, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/249,234

(22) Filed: Aug. 26, 2016

(65) Prior Publication Data

US 2017/0128504 A1 May 11, 2017

Related U.S. Application Data

(63) Continuation of application No. 14/345,642, filed as application No. PCT/KR2012/007555 on Sep. 20, 2012, now Pat. No. 9,717,768.

(30) Foreign Application Priority Data

Sep. 20, 2011 (KR) ........................ 10-2011-0094648

(51) Int. Cl.
| | |
|---|---|
| *A61K 35/76* | (2015.01) |
| *A23K 20/147* | (2016.01) |
| *A23K 20/10* | (2016.01) |
| *A23K 20/195* | (2016.01) |
| *A23K 50/10* | (2016.01) |
| *A23K 50/30* | (2016.01) |
| *A23K 50/75* | (2016.01) |
| *C12N 7/00* | (2006.01) |
| *C12R 1/92* | (2006.01) |
| *A01N 63/00* | (2006.01) |
| *C12R 1/91* | (2006.01) |

(52) U.S. Cl.
CPC ............. *A61K 35/76* (2013.01); *A01N 63/00* (2013.01); *A23K 20/10* (2016.05); *A23K 20/147* (2016.05); *A23K 20/195* (2016.05); *A23K 50/10* (2016.05); *A23K 50/30* (2016.05); *A23K 50/75* (2016.05); *C12N 7/00* (2013.01); *C12R 1/91* (2013.01); *C12N 2795/10321* (2013.01); *C12N 2795/10331* (2013.01); *C12N 2795/10332* (2013.01)

(58) Field of Classification Search
None
See application file for complete search history.

(56) References Cited

U.S. PATENT DOCUMENTS

| | | | |
|---|---|---|---|
| 6,485,902 B2 | 11/2002 | Waddell et al. | |
| 6,942,858 B1 | 9/2005 | Ghanbari et al. | |
| 2010/0135962 A1* | 6/2010 | Kang .................. | C07K 14/005 424/93.6 |
| 2010/0158870 A1 | 6/2010 | Kang et al. | |
| 2010/0166709 A1 | 7/2010 | Kang et al. | |
| 2011/0052541 A1 | 3/2011 | Shin et al. | |
| 2011/0052542 A1 | 3/2011 | Shin et al. | |
| 2011/0052543 A1 | 3/2011 | Shin et al. | |
| 2011/0052544 A1 | 3/2011 | Shin et al. | |

FOREIGN PATENT DOCUMENTS

| | | |
|---|---|---|
| KR | 10-2009-0030386 A | 3/2009 |
| KR | 10-2010-0075263 A | 7/2010 |
| KR | 1020140015896 * | 4/2016 |
| WO | 2010-074433 A2 | 7/2010 |

OTHER PUBLICATIONS

English MT.Kyoung, W.L. 2016.Fermented extract of Gastrodia elata with excellent antioxidant activity and taste and manufacturing method thereof. Korean Patent Application No. 1020140015896. Pub. Date: Apr. 5, 2016. pp. 1-26. specif. p. 8, para. 5.*
Ackermann, H.-W., "Frequency of morphological phage descriptions in the year 2000," Arch Virol 146: 843-857, 2001.
Nnalue et al., "Lysogenization of *Salmonella choleraesuis* by phage 14 increases average length of O-antigen chains, serum resistance and intraperitoneal mouse virulence," Microbial Pathogenesis 8: 393-402, 1990.
O'Flynn et al., "The newly isolated lytic bacteriophages st104a and st104b are highly virulent against *Salmonella enterica*," Journal of Applied Microbiology 101:251-259, 2006.

* cited by examiner

*Primary Examiner* — Renee Claytor
*Assistant Examiner* — Sharon M. Papciak
(74) *Attorney, Agent, or Firm* — Cooley LLP

(57) ABSTRACT

The present invention relates to a bacteriophage having a specific bactericidal activity against *Salmonella*, a composition for the prevention or treatment of infectious diseases comprising the bacteriophage as an active ingredient, an antibiotic comprising the bacteriophage as an active ingredient, an animal feed or drinking water comprising the bacteriophage as an active ingredient, and a sanitizer or cleaner comprising the bacteriophage as an active ingredient. The bacteriophage of the present invention has a specific bactericidal activity against *Salmonella choleraesuis*, *Salmonella typhimurium*, *Salmonella derby*, *Salmonella infantis* or *Salmonella newport* with no influences on beneficial bacteria, as well as excellent acid- and heat-resistance and desiccation tolerance.

12 Claims, 9 Drawing Sheets

Specification includes a Sequence Listing.

[FIG. 1]
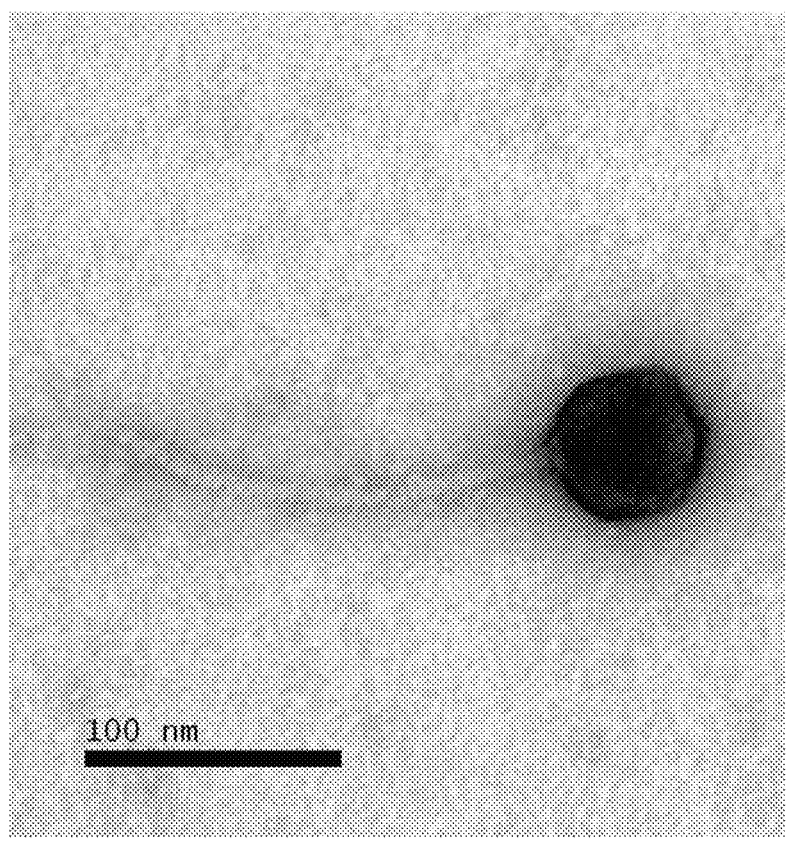

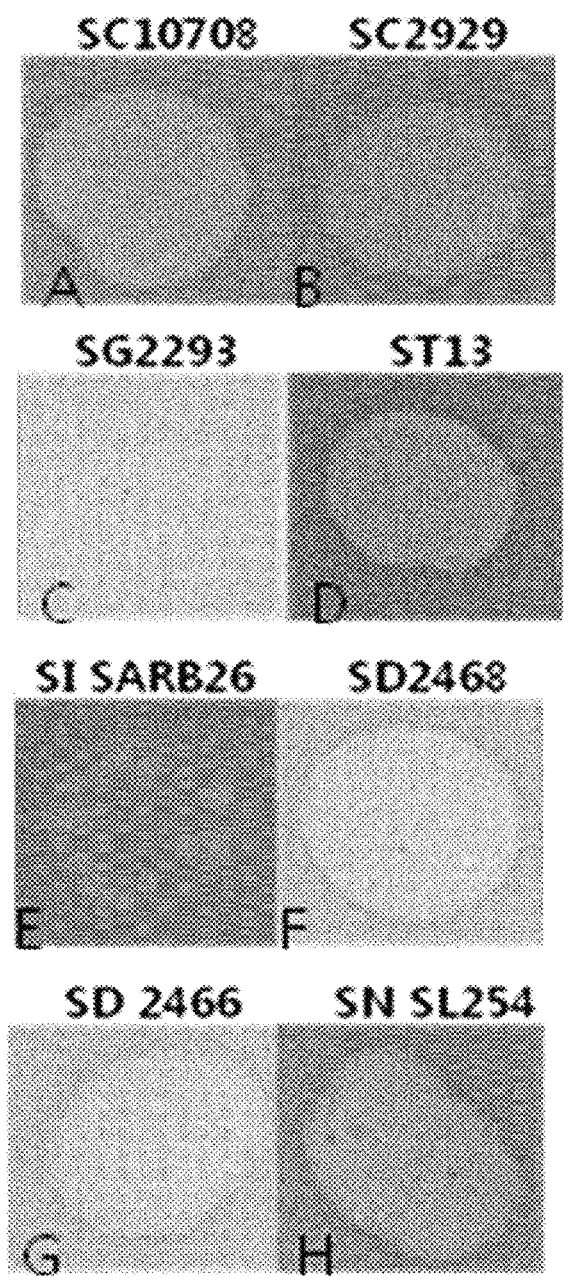
[FIG. 2]

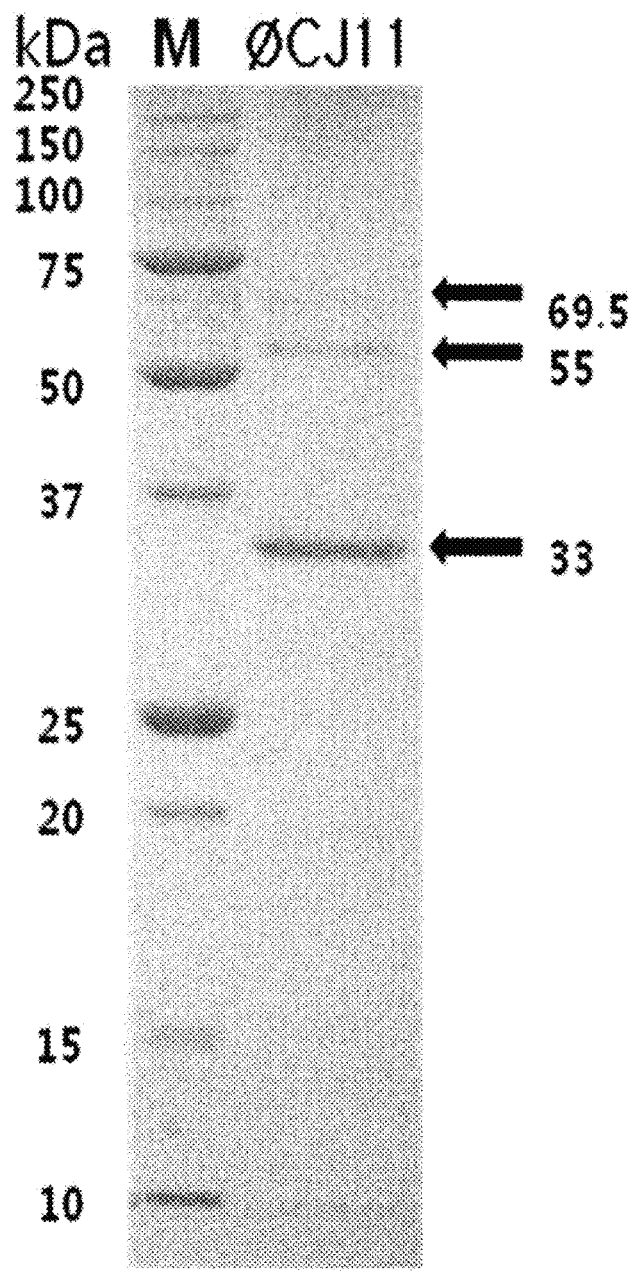
[FIG. 3]

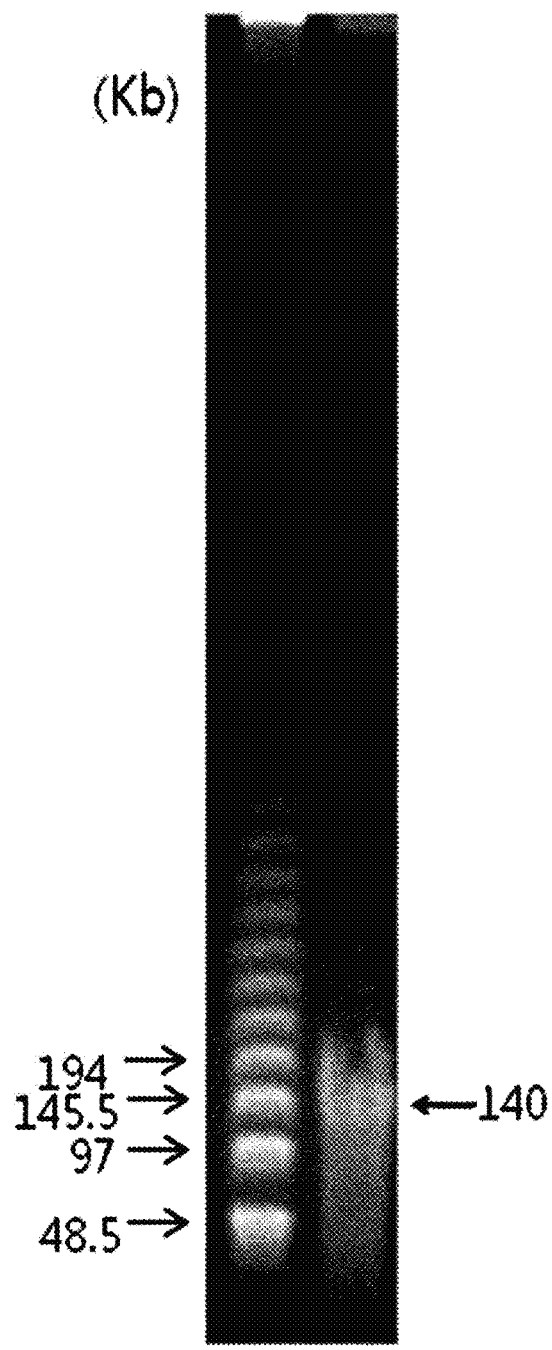
[FIG. 4]

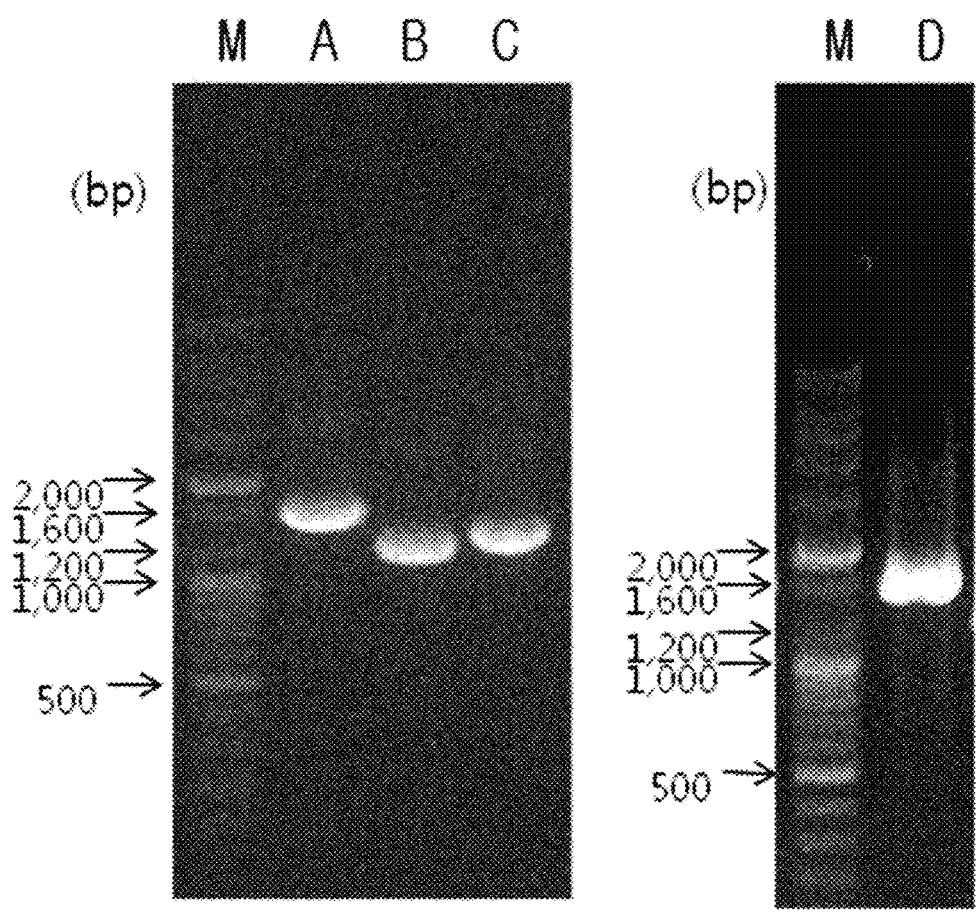
[FIG. 5]

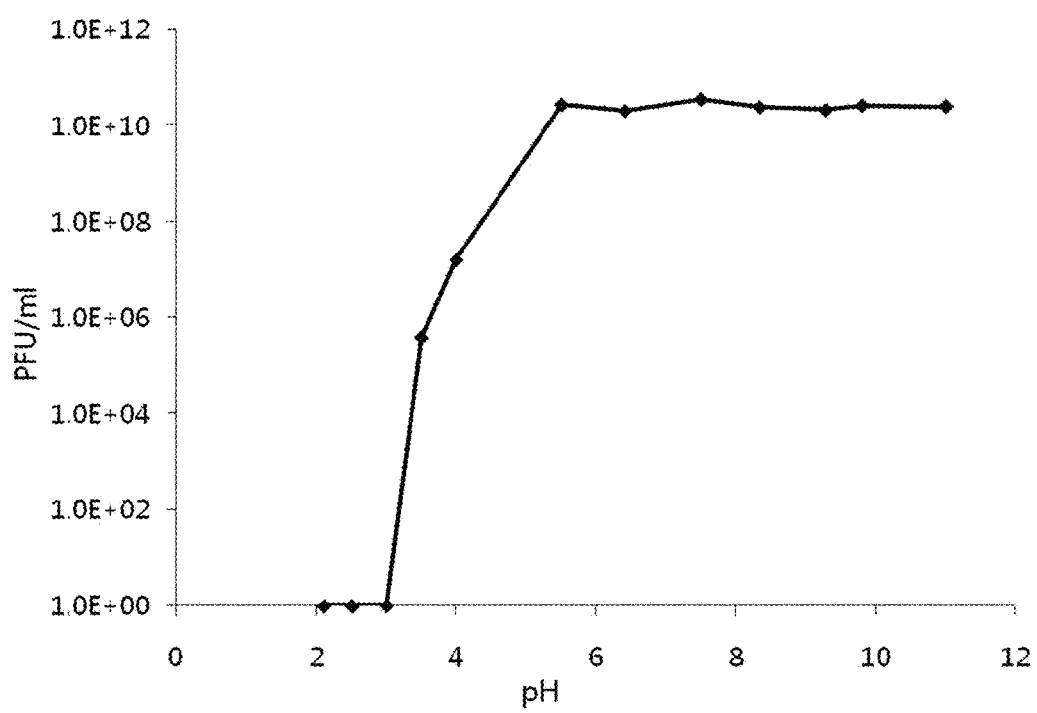
[FIG. 6]

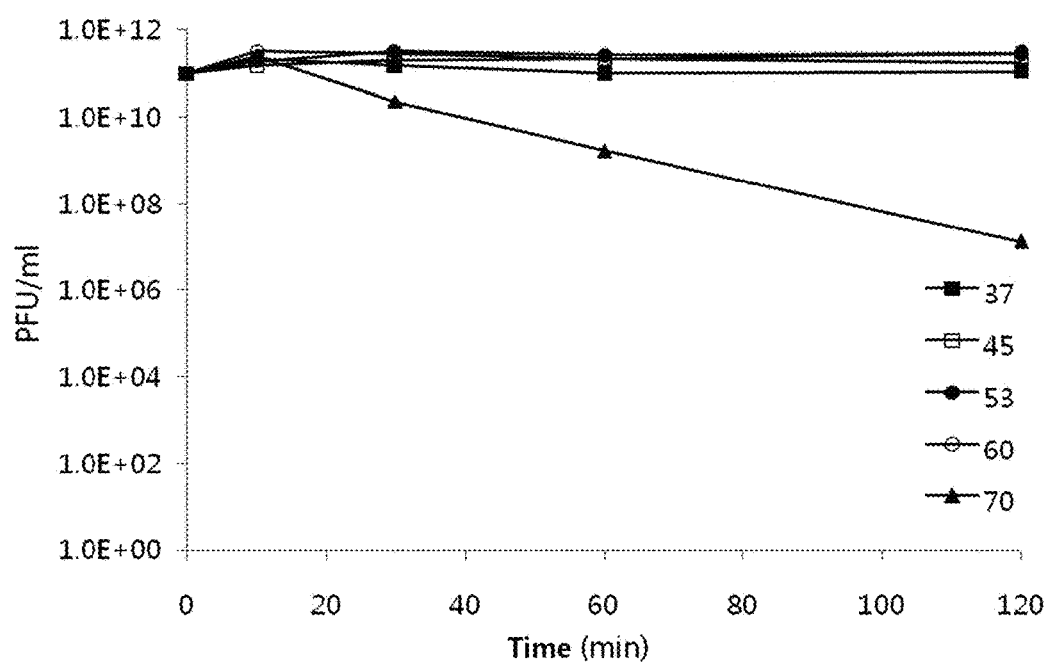
[FIG. 7]

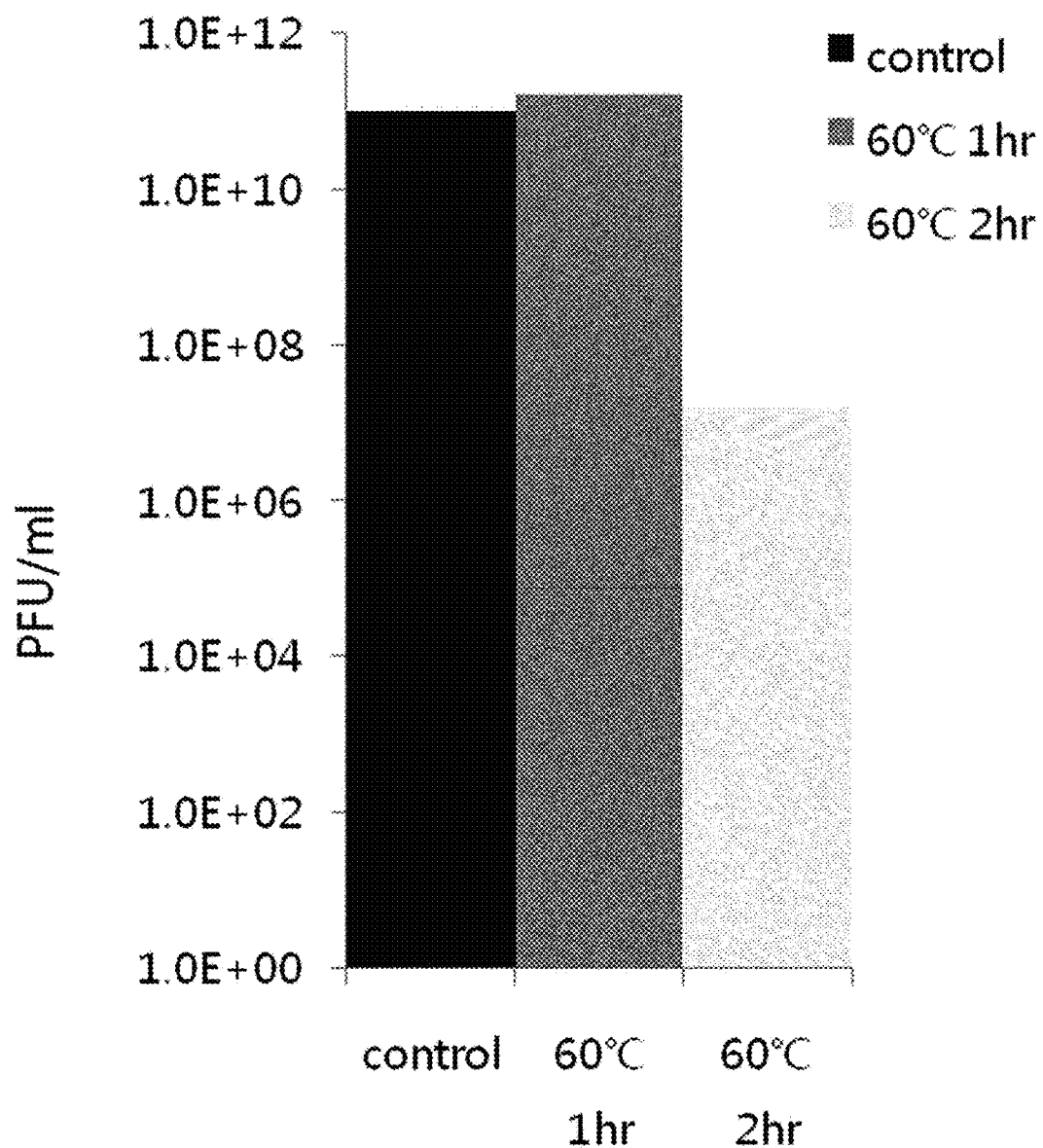
[FIG. 8]

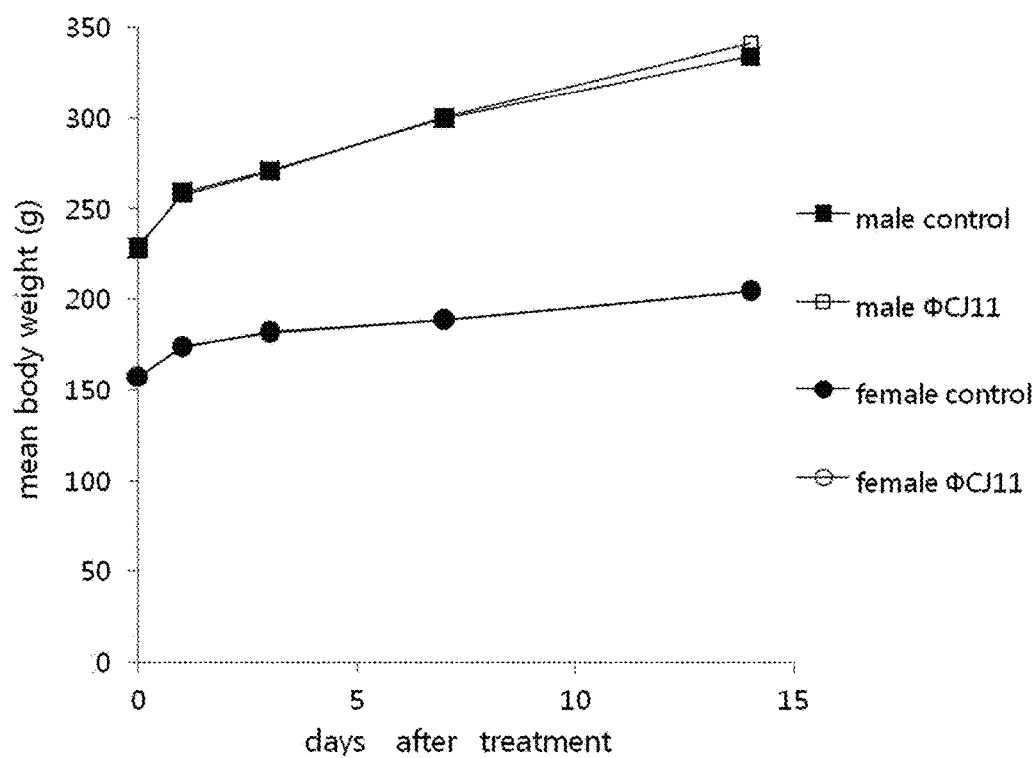
[FIG. 9]

BACTERIOPHAGE AND ANTIBACTERIAL COMPOSITION COMPRISING THE SAME

CROSS-REFERENCE TO RELATED APPLICATIONS

This application is a continuation of U.S. application Ser. No. 14/345,642, filed Mar. 18, 2014, which is a U.S. national phase application of International PCT Patent Application No. PCT/KR2012/007555, filed Sep. 20, 2012, which claims priority to Korean Patent Application No. 10-2011-0094648, filed Sep. 20, 2011. The foregoing applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_025_01US_ST25.txt. The text file is 11 KB, was created on Aug. 26, 2016, and is being submitted electronically via EFS-Web.

TECHNICAL FIELD

The present invention relates to a novel bacteriophage and an antibacterial composition comprising the same.

BACKGROUND ART

*Salmonella* has an average genomic GC content of 50-52%, which is similar to that of *Escherichia coli* and *Shigella*. The genus *Salmonella* is a pathogenic microorganism that causes infections in livestock as well as in humans. Serological division has it that *Salmonella enterica*, a species of *Salmonella* bacterium, has a variety of serovars including *Salmonella gallinarum*, *Salmonella pullorum*, *Salmonella typhimurium* (ST), *Salmonella enteritidis* (SE), *Salmonella typhi*, *Salmonella choleraesuis* (SC), *Salmonella derby* (SD). Of them, *choleraesuis* and *derby* are swine-adapted pathogens, *gallinarum* and *pullorum* are fowl-adapted pathogens, *typhimurium* and enteritis are pathogenic for humans and animals, and *typhi* is a human-adapted pathogen, all of which cause illness in their respective species, resulting in tremendous damage to farmers and consumers (Zoobises Report; United Kingdom 2003).

Recently, implementation of HACCP (Hazard analysis and critical control points) has become a mandatory requirement for all slaughterhouses in Korea as of Jul. 1, 2003, because of the high risk of contamination in the course of manufacturing livestock products with *salmonella*, which causes direct damage to pigs, and meat hygiene and is found in the digestive tract of pigs (Jae-gil Yeh. Characterization and Counterplan of Salmonellosis in Pigs. Monthly Magazine of Pig Husbandry. 2004).

Paratyphoid, the acute or chronic infectious disease in the digestive tract of pig caused by *salmonella* infection, is characterized by gastroenteritis and septicaemia and mainly occurs during the fatting period. In particular, some of pathogenic bacteria that cause this disease can cause food poisoning in humans through meat ingestion, and thus it is a disease having major public health importance. A variety of types of *salmonella* bacteria can be pathogenic. Among them, *Salmonella choleraesuis* and *Salmonella typhisuis* known to cause hog cholera are the major causes of acute *salmonella* septicaemia. Acute enteritis occurs during the fattening period, and is accompanied by irregular appetite, severe watery diarrhea, high fever, loss of vitality, pneumonia, and nervous signs. Discoloration of the skin may occur in some severe cases. *Salmonella typhimurium*, *Salmonella enteritidis*, and *Salmonella derby* are the major causes of chronic enteritis.

Salmonellosis is caused by oral route through feed or water contaminated with *salmonella*, and thus these routes should be prevented. Contaminated feed, raw materials or water, or adult pigs carrying the pathogen can be major sources of infection. During the acute period of infection, pigs shed up to $10^6$ *Salmonella choleraesuis* or $10^7$ *Salmonella typhimurium* per gram of feces. However, many experimental infections reported successful disease reproduction with a dose of $10^8$ to $10^{11}$ *Salmonella*. In an experiment injecting $10^3$ *Salmonella* into pigs, the injected pigs showed no symptoms of the disease, but other pigs raised in the same pen showed typical clinical symptoms. These results indicate that a large amount of *salmonella* grow in naturally infected pigs, resulting in the infection of other pigs (Jung-Bok Lee. Control of the Recent Outbreaks of Porcine *Salmonella* and Proliferative Enteropathy. Korea Swine Association. 2009).

At present, severe viral infections such as Porcine Reproductive and Respiratory Syndrome (PRRS) and Porcine Circovirus (PCV2) have been causing tremendous economic losses to the swine industry in Korea, and thus disease management has been focused on these diseases. Since these bacterial diseases may cause tremendous damage comparable to that caused by viral diseases beginning with a ban on the use of in-feed antibiotics and an investigation of disease occurrence or disease management should be performed in advance (Jung-Bok Lee. Control of the Recent Outbreaks of Porcine *Salmonella* and Proliferative Enteropathy, Infectious Disease Laboratory, College of Veterinary Medicine, Konkuk University, Livestock Product Safety, 2010) (Robert W. Wills, Veterinary Microbiology, 1999). Meanwhile, bacteriophage, also called phage, is a specialized type of virus that infects only particular bacteria and controls the growth of bacteria, and can self-replicate only inside the host bacteria. After the discovery of bacteriophages, a great deal of faith was initially placed in their use for infectious-disease therapy. However, when broad spectrum antibiotics came into common use, bacteriophages were seen as unnecessary due to a specific target spectrum. Antibiotics or antimicrobial agents have been widely used for the treatment of infectious diseases caused by bacterial infection. Nevertheless, the misuse and overuse of antibiotics resulted in rising concerns about antibiotic resistance and the harmful effects of residual antibiotics in foods. However, the removal of current in-feed antibiotics might increase occurrence of bacterial diseases including salmonellosis that have been controlled by antibiotics, as expected in the experiment data or from other countries. Thus, there is an urgent need to establish a detailed practical guideline for *salmonella* management (Jung-Bok Lee. Control of the Recent Outbreaks of Porcine *Salmonella* and Proliferative Enteropathy, Infectious Disease Laboratory, College of Veterinary Medicine, Konkuk University, Livestock Product Safety. 2010).

These growing concerns have led to a resurgence of interest in bacteriophage. Seven bacteriophages for control of *E. coli* O157:H7 are disclosed in U.S. Pat. No. 6,485,902 (2002) and two bacteriophages for control of various microorganisms are disclosed in U.S. Pat. No. 6,942,858 (issued to Nymox in 2005). Many companies have been actively trying to develop various products using bacteriophages. EBI food system (Europe) developed a food additive for preventing food poisoning caused by *Listeria monocytogenes*, named Listerix-P100, which is the first bacteriophage product approved by the USFDA. A phage-based product, LMP-102 was also developed as a food additive against *Listeria monocytogenes*, approved as GRAS (Generally Regarded As Safe). In 2007, a phage-based wash produced by OmniLytics was developed to prevent *E. coli* 0157 contamination of beef during slaughter, approved by USDA's Food Safety and Inspection Service (FSIS). In Europe, *Clostridium sporogenes* phage NCIMB 30008 and *Clostridium* tyrobutiricum phage NCIMB 30008 were registered as feed preservative against *Clostridium* contamination of feed in 2003 and 2005, respectively. Such studies show that research into bacteriophages for the control of antibiotic-unsusceptible bacteria and contamination of livestock products by zoonotic pathogens is presently ongoing.

However, most of the phage biocontrol studies have focused on the control of *E. coli, Listeria*, and *Clostridium*. *Salmonella* is also a zoonotic pathogen, and damages due to this pathogen are not reduced. As mentioned above, since *Salmonella* exhibits multiple drug resistances, nationwide antimicrobial resistance surveillance has been conducted in Korea under the Enforcement Decree of the Act on the Prevention of Contagious Disease (Executive Order 16961), Enforcement Ordinance of the Act on the Prevention of Contagious Disease (Ministry of Health and Welfare's Order 179), and Organization of the National Institute of Health (Executive Order 17164). Accordingly, there is a need for the development of bacteriophages to control *Salmonella*.

DISCLOSURE

Technical Problem

In order to overcome problems occurring upon the misuse or overuse of broad spectrum antibiotics, such as drug resistant bacteria and drug residues in foods, the present inventors isolated a bacteriophage from natural sources, in which the bacteriophage has a specific bactericidal activity against *salmonella* causing major diseases in livestock. As a result, they found that the bacteriophage has a specific bactericidal activity against *Salmonella choleraesuis* (SC), *Salmonella typhimurium* (ST), *Salmonella* derby (SD), *Salmonella infantis* (SI) and *Salmonella newport* (SN) with no influences on beneficial bacteria, in addition to showing excellent acid- and heat-resistance, as identified for the morphological, biochemical and genetic properties thereof. Further, they found that the bacteriophage can be applied to compositions for the prevention or treatment of *Salmonella typhimurium*-mediated diseases, such as livestock *salmonellosis* and *Salmonella* food poisoning, and to various products for the effective prevention and control of *Salmonella* bacteria proliferation, including livestock feed additives, drinking water for livestock, barn sanitizers, and cleaners for meat products, thereby completing the present invention.

Technical Solution

An object of the present invention is to provide a novel bacteriophage having a bactericidal activity against *Salmonella choleraesuis*.

Another object of the present invention is to provide a composition for the prevention or treatment of infectious diseases caused by *Salmonella choleraesuis, Salmonella typhimurium, Salmonella derby, Salmonella infantis* or *Salmonella newport*, comprising the bacteriophage as an active ingredient.

Still another object of the present invention is to provide an antibiotic, comprising the bacteriophage as an active ingredient.

Still another object of the present invention is to provide an animal feed or drinking water comprising the bacteriophage as an active ingredient.

Still another object of the present invention is to provide a sanitizer or cleaner, comprising the bacteriophage as an active ingredient.

Still another object of the present invention is to provide a method for preventing or treating of infectious diseases caused by *Salmonella choleraesuis, Salmonella typhimurium, Salmonella derby, Salmonella infantis* or *Salmonella newport*, using the bacteriophage or the composition.

Advantageous Effects

The novel bacteriophage of the present invention has a specific bactericidal activity against *Salmonella choleraesuis, Salmonella typhimurium, Salmonella derby, Salmonella infantis* or *Salmonella newport* with no influences on beneficial bacteria, and excellent acid- and heat-resistance and desiccation tolerance. Therefore, the novel bacteriophage can be used for the prevention or treatment of *salmonellosis* or *salmonella* food poisoning, which is an infectious disease caused by *Salmonella choleraesuis, Salmonella typhimurium, Salmonella derby, Salmonella infantis* or *Salmonella newport*, and also widely used in animal feeds, drinking water for livestock, sanitizers, and cleaners.

DESCRIPTION OF DRAWINGS

FIG. 1 is an electron microscopy photograph of ΦCJ11, which belongs to the family Siphoviridae of morphotype B1, characterized by an isometric capsid and a long non-contractile tail;

FIG. 2 is a photograph showing the formation of ΦCJ11 plaques in a lawn of *salmonella* bacteria, in which (A,B; SC, C; SG, D; ST, E; SI, F,G; SD, H; SN), plaque formation was observed in lawns of SC, ST, SI, SD and SN, but not in lawns of SG;

FIG. 3 is the result of SDS-PAGE of the isolated bacteriophage ΦCJ11, in which the major proteins were detected at 33 kDa, 55 kDa and 69.5 kDa, and Precision plus protein standard (BIO-RAD) was used as a marker;

FIG. 4 is the result of PFGE of the isolated bacteriophage ΦCJ11, in which a total genome size of ΦCJ11 was approximately 140 kbp, and the CHEF DNA Size Standard Lambda Ladder (Bio-Rad) was used as a DNA size marker;

FIG. 5 is the result of PCR, performed using each primer set for the ΦCJ11 genomic DNA, in which A; a primer set of SEQ ID NOs. 5 and 6, B; a primer set of SEQ ID NOs. 7 and 8, C; a primer set of SEQ ID NOs. 9 and 10, and D; a primer set of SEQ ID NOs. 11 and 12, and all of A, B, C and D lanes had PCR products of approximately 1 kbp or more to 2 kbp or less;

FIG. 6 is the result of acid-resistance assay on the bacteriophage ΦCJ11, showing the number of surviving bacteriophage at pH 2.1, 2.5, 3.0, 3.5, 4.0, 5.5, 6.4, 6.9, 7.4, 8.0, 9.0, 9.8 and 11.0, in which the bacteriophage ΦCJ11 did not lose its activity until pH 5.5, but the bacteriophage ΦCJ11 showed reduced activity at pH 4 and pH 3.5, and completely lost its activity at pH 3.0 or lower, as compared to a control;

FIG. 7 is the result of heat-resistance assay on the bacteriophage ΦCJ11, showing the number of surviving bacteriophage at 37, 45, 53, 60, and 70° C. for 0, 10, 30, 60 and 120 minutes, in which the bacteriophage ΦCJ11 maintained its activity even though exposed to 60° C. for up to 2 hours;

FIG. 8 is the result of desiccation tolerance assay on the bacteriophage ΦCJ11 dried with the aid of a SpeedVac concentrator, in which when titer changes under the dry condition were measured in comparison with pre-drying titers, the activity was maintained at 60° C. for up to 1 hour; and FIG. 9 is the results of body weight changes due to toxicity after single oral administration of Sprague-Dawley rats with ΦCJ11, in which observation of body weight changes before and 1, 3, 7, 10 and 14 days after administration with ΦCJ11 showed no significant changes in comparison with the control group (■; male control, □; ΦCJ11 male, ●; female control, ○; ΦCJ11 female).

BEST MODE

In one aspect to achieve the above objects, the present invention provides a novel bacteriophage having a specific bactericidal activity against *Salmonella choleraesuis, Salmonella typhimurium, Salmonella derby, Salmonella infantis* or *Salmonella newport*.

The present inventors collected fecal and sewage samples from swinery, and isolated therefrom bacteriophages that can lyse the host cell SC. They were also found that these bacteriophages can lyse ST, SD, SI and SN (FIG. 2 and Table 1). A morphological examination under an electron microscope confirmed that the bacteriophage (ΦCJ11) belongs to the family Siphoviridae of morphotype B1 (FIG. 1). Further, the bacteriophage ΦCJ11 was found to have major structural proteins of approximately 69.5 kDa, 55 kDa and 33 kDa, as measured by a protein pattern analysis (FIG. 3), and a genome analysis showed that ΦCJ11 has a total genome size of approximately 97-145.5 kbp (FIG. 4). Furthermore, the results of analyzing its genetic features showed that the bacteriophage includes nucleic acid molecules represented by SEQ ID NOs. 1 to 4 within the total genome (Example 6). Based on SEQ ID NOs. 1 to 4, genetic similarity with other species was compared. It was found that the bacteriophage showed very low genetic similarity with the known bacteriophages, indicating that the bacteriophage is a novel bacteriophage (Table 2). For more detail analysis of genetic features, the ΦCJ11-specific primer sets, namely, SEQ ID NOs. 5 and 6, SEQ ID NOs. 7 and 8, SEQ ID NOs. 9 and 10, and SEQ ID NOs. 11 and 12 were used to perform PCR. Each PCR product was found to have a size of 1.4 kbp, 1.2 kbp, 1.25 kbp and 1.5 kbp (FIG. 5).

Meanwhile, when SC, ST, SD, SI and SN were infected with ΦCJ11, the phage plaques (clear zone on soft agar created by host cell lysis of one bacteriophage) were observed (FIG. 2). The stability of ΦCJ11 was examined under various temperature and pH conditions, resulting in that ΦCJ11 stably maintains in a wide range of pH environments from pH 3.5 to pH 11.0 (FIG. 6) and in high temperature environments from 37° C. to 70° C. (FIG. 7), and even after desiccation (FIG. 8). Also, the wild-type strains SC, ST, SD, SI and SN were also found to fall within the host cell range of ΦCJ11 (Table 3).

Finally, the results of dermal and ocular irritation tests on ΦCJ11 in specific-pathogen-free (SPF) New Zealand White rabbits showed that the primary irritation index (PII) was 0.33, indicating no irritant, and the index of acute ocular irritation (IAOI) was 0 in washing and non-washing groups during the whole experimental periods, indicating no irritant. The results of oral administration of ΦCJ11 showed no changes in weight gain (FIG. 9). As well, mortality, general symptoms (Table 4) and organ abnormality (Table 5) were not observed, indicating no toxicity.

Accordingly, the present inventors designated the bacteriophage as "Bacteriophage ΦCJ11", in which the bacteriophage was isolated from fecal and sewage samples from swinery and has a specific bactericidal activity against SC, ST, SD, SI and SN and the above characteristics, and deposited at the Korean Culture Center of Microorganisms (361-221, Honje 1, Seodaemun, Seoul) on Sep. 9, 2011 under accession number KCCM11208P.

In another aspect to achieve the above objects, the present invention provides a composition for the prevention or treatment of infectious disease caused by one or more *Salmonella* bacteria selected from the group consisting of *Salmonella choleraesuis, Salmonella typhimurium, Salmonella derby, Salmonella infantis* and *Salmonella newport*, comprising the bacteriophage as an active ingredient.

Having specific bactericidal activity against *Salmonella choleraesuis, Salmonella typhimurium, Salmonella derby, Salmonella infantis* and *Salmonella newport*, the bacteriophage of the present invention may be used for the purpose of preventing or treating the diseases caused by these bacteria. Preferably, examples of the infectious diseases include porcine *salmonellosis* and *Salmonella* food poisoning caused by *Salmonella choleraesuis* or *Salmonella typhimurium*, and acute or chronic porcine enteritis caused by *Salmonella* derby, *Salmonella infantis, Salmonella newport*, but are not limited thereto.

As used herein, the term "*salmonellosis*" refers to symptoms following *salmonella* infection, such as fever, headache, diarrhea, and vomiting. That is, *salmonellosis* is an infection with bacteria of the genus *Salmonella*, which is defined with two clinical forms: an acute septicemic form that resembles typhoid fever and an acute gastroenteritis, including enteritis, food poisoning, and acute septicemia.

As used herein, the term "prevention" means all of the actions in which disease progress is restrained or retarded by the administration of the composition.

As used herein, the term "treatment" means all of the actions in which the condition has taken a turn for the better or been restrained or modified favorably by the administration of the composition.

The composition of the present invention includes ΦCJ11 in an amount of $1 \times 10^2$ to $1 \times 10^{12}$ PFU/mL, and preferably in an amount of $1 \times 10^6$ to $1 \times 10^{10}$ PFU/mL.

On the other hand, the composition of the present invention may further include a pharmaceutically acceptable carrier.

As used herein, the term "pharmaceutically acceptable carrier" refers to a carrier or diluent that does not cause significant irritation to an organism and does not abrogate the biological activity and properties of the administered compound. For formulation of the composition into a liquid preparation, a pharmaceutically acceptable carrier which is sterile and biocompatible may be used such as saline, sterile water, Ringer's solution, buffered physiological saline, albumin infusion solution, dextrose solution, maltodextrin solution, glycerol, ethanol, and mixtures of one or more thereof. If necessary, other conventional additives such as antioxidants, buffers, and bacteriostatic agents may be added. Further, diluents, dispersants, surfactants, binders and lubricants may be additionally added to the composition to prepare injectable formulations such as aqueous solutions, suspensions, and emulsions, or oral formulations such as pills, capsules, granules, or tablets.

The prophylactic or therapeutic compositions of the present invention may be applied or sprayed to the afflicted area, or administered by oral or parenteral routes. The parenteral administration may include intravenous, intraperitoneal, intramuscular, subcutaneous or topical administration.

The dosage suitable for applying, spraying, or administrating the composition of the present invention will depend upon a variety of factors including formulation method, the mode of administration, the age, weight, sex, condition, and diet of the patient or animal being treated, the time of administration, the route of administration, the rate of excretion, and reaction sensitivity. A physician or veterinarian having ordinary skill in the art can readily determine and prescribe the effective amount of the composition required.

Examples of the oral dosage forms including the composition of the present invention as an active ingredient include tablets, troches, lozenges, aqueous or emulsive suspensions, powder or granules, emulsions, hard or soft capsules, syrups, or elixirs. For formulation such as tablets and capsules, the following are useful: a binder such as lactose, saccharose, sorbitol, mannitol, starch, amylopectin, cellulose or gelatin; an excipient such as dicalcium phosphate; a disintegrant such as corn starch or sweet potato starch; and a lubricant such as magnesium stearate, calcium stearate, sodium stearylfumarate, or polyethylene glycol wax. For capsules, a liquid carrier such as lipid may be further used in addition to the above-mentioned compounds.

The parenteral dosage forms including the composition of the present invention as an active ingredient may be formulated into injections via subcutaneous, intravenous, or intramuscular routes, suppositories, or sprays inhalable via the respiratory tract, such as aerosols. Injection forms may be prepared by dissolving or suspending the composition of the present invention, together with a stabilizer or a buffer, in water and loading the solution or suspension onto ampules or vial unit forms. For sprays, such as aerosols, a propellant for spraying a water-dispersed concentrate or wetting powder may be used in combination with an additive.

In still another aspect to achieve the above objects, the present invention provides an antibiotic comprising the bacteriophage as an active ingredient.

As used herein, the term "antibiotic" means any drug that is applied to animals to kill pathogens, and used herein as a general term for antiseptics, bactericidal agents and antibacterial agents. The animals are mammals including human. The bacteriophage of the present invention, unlike the conventional antibiotics, has a high specificity to *Salmonella* so as to kill the specific pathogens without affecting beneficial bacteria, and does not induce drug resistance so that it can be provided as a novel antibiotic with a comparatively long life cycle.

In still another aspect to achieve the above objects, the present invention provides an animal feed or drinking water comprising the bacteriophage as an active ingredient.

In-feed antibiotics used in the livestock and fishery industries are intended to prevent infections. However, most of the currently available in-feed antibiotics are problematic in that they are apt to induce the occurrence of resistant strains and may be transferred to humans, due to remaining in livestock products. The uptake of such residual antibiotics may make human pathogens resistant to antibiotics, resulting in the spread of diseases. In addition, since there are a variety of in-feed antibiotics, the increasing global emergence of multidrug-resistant strain is a serious concern. Therefore, the bacteriophage of the present invention can be used as an in-feed antibiotic that is more eco-friendly and able to solve the above problems.

The animal feed of the present invention may be prepared by adding the bacteriophage directly or in separate feed additive form to an animal feed. The bacteriophage of the present invention may be contained in the animal feed as a liquid or in a solid form, preferably in a dried powder. The drying process may be performed by air drying, natural drying, spray drying, and freeze-drying, but is not limited thereto. The bacteriophage of the present invention may be added as a powder form in an amount of 0.05 to 10% by weight, preferably 0.1 to 2% by weight, based on the weight of animal feed. The animal feed may also include other conventional additives for long-term preservation, in addition to the bacteriophage of the present invention.

The feed additive of the present invention may additionally include other non-pathogenic microorganisms. The available additional microorganism may be selected from the group consisting of *Bacillus subtilis* that can produce protease, lipase and invertase, *Lactobacillus* sp. strain that can exert physiological activity and a function of decomposing under anaerobic conditions, such as in the stomach of cattle, filamentous fungi including *Aspergillus oryzae* (J Animal Sci 43:910-926, 1976) that increases the weight of domestic animals, enhances milk production and helps the digestion and absorptiveness of feeds, and yeast including *Saccharomyce scerevisiae* (J Anim Sci 56:735-739, 1983).

The feed including ΦCJ11 of the present invention may include plant-based feeds, such as grain, nut, food byproduct, seaweed, fiber, drug byproduct, oil, starch, meal, and grain byproduct, and animal-based feeds such as protein, inorganic matter, fat, mineral, fat, single cell protein, zooplankton, and food waste, but is not limited thereto.

The feed additive including ΦCJ11 of the present invention may include binders, emulsifiers, and preservatives for the prevention of quality deterioration, amino acids, vitamins, enzymes, probiotics, flavorings, non-protein nitrogen, silicates, buffering agents, coloring agents, extracts, and oligosaccharides for efficiency improvement, and other feed premixtures, but is not limited thereto.

Further, the supply of drinking water mixed with the bacteriophage of the present invention can reduce the number of *Salmonella* bacteria in the intestine of livestock, thereby obtaining *Salmonella*-free livestock.

In still another aspect to achieve the above objects, the present invention provides a sanitizer or cleaner comprising the bacteriophage as an active ingredient.

In still another aspect to achieve the above objects, the present invention provides a method for treating infectious diseases caused by *Salmonella choleraesuis, Salmonella typhimurium, Salmonella derby, Salmonella infantis* or *Salmonella newport* using the bacteriophage or the composition.

In detail, the therapeutic method of the present invention comprises the step of administering a pharmaceutically effective amount of the bacteriophage or the composition to an individual having infectious diseases caused by *Salmonella choleraesuis, Salmonella typhimurium, Salmonella derby, Salmonella infantis* or *Salmonella newport*.

The bacteriophage or the composition of the present invention may be administered in the form of a pharmaceutical formulation into animals or may be ingested as a mixture with animal feed or drinking water by animals and preferably as a mixture with animal feed.

As long as it reaches target tissues, any route, whether oral or parenteral, may be taken for administering the bacteriophage or the composition of the present invention. In detail, the composition of the present invention may be administered in a typical manner via any route such as oral, rectal, topical, intravenous, intraperitoneal, intramuscular, intraarterial, transdermal, intranasal, and inhalation routes.

It will be obvious to those skilled in the art that the total daily dose of the bacteriophage or the composition of the present invention to be administered by the therapeutic method should be determined through appropriate medical judgment by a physician. Preferably, the therapeutically effective amount for given patients may vary depending on various factors well known in the medical art, including the kind and degree of the response to be achieved, the patient's condition such as age, body weight, state of health, sex, and diet, time and route of administration, the secretion rate of the composition, the time period of therapy, concrete compositions according to whether other agents are used therewith or not, etc.

MODE FOR INVENTION

Hereinafter, the present invention will be described in more detail with reference to Examples. However, these Examples are for illustrative purposes only, and the invention is not intended to be limited by these Examples.

Example 1: *Salmonella* Bacteriophage Isolation

Example 1-1: Bacteriophage Screening and Single Bacteriophage Isolation 50 mL of sample from swinery and sewage effluent was transferred to a centrifuge tube, and centrifuged at 4000 rpm for 10 minutes. Then, the supernatant was filtered using a 0.45 μm filter. 18 mL of sample filtrate was mixed with 150 μl of *Salmonella choleraesuis* ("SC") shaking culture medium ($OD_{600}$=2) and 2 mL of 10× Luria-Bertani medium (tryptone 10 g/L, yeast extract 5 g/L and NaCl 10 g/L: LB medium). The mixture was cultured at 37° C. for 18 hours, and the culture medium was centrifuged at 4000 rpm for 10 minutes. The supernatant was filtered using a 0.2 μm filter. 3 mL of 0.7% agar (w/v) and 150 μl of SC shaking culture medium ($OD_{600}$=2) were mixed, and plated onto LB plate ("top-agar"), and allowed to solidify. 10 μl of the culture filtrate was spread thereon, and cultured for 18 hours at 37° C., and the titration of phage lysate was performed on the top-agar, called soft agar overlay method.

The sample culture medium containing the phage lysate was properly diluted, and mixed with 150 μl of SC shaking culture medium ($OD_{600}$=2), followed by soft agar overlay method, so that single plaques were obtained. A single plaque represents one bacteriophage and thus, for isolation of single bacteriophages, one phage plaque was added to 400 μl of SM solution (NaCl, 5.8 g/L, $MgSO_4 7H_2O$, 2 g/L, 1 M Tris-Cl (pH 7.5) 50 ml/L), and left for 4 hours at room temperature to isolate single bacteriophages. To purify the bacteriophage in large quantities, 100 μl of supernatant was taken from the single bacteriophage solution, and mixed with 12 mL of 0.7% agar and 500 μl of SC shaking culture medium, followed by soft agar overlay method on LB plate having a diameter of 150 mm. When lysis was completed, 15 mL of SM solution was added to the plate. The plate was gently shaken for 4 hours at room temperature to elute the bacteriophages from the top-agar. The SM solution containing the eluted bacteriophages was recovered, chloroform was added to a final volume of 1%, and mixed well for 10 minutes. The solution was centrifuged at 4000 rpm for 10 minutes. The obtained supernatant was filtered using a 0.45 μm filter, and stored in the refrigerator.

Example 1-2: Large-Scale Batches of Bacteriophage

The selected bacteriophages were cultured in large quantities using SC. SC was shaking-cultured, and an aliquot of $1.5×10^{10}$ cfu (colony forming units) was centrifuged at 4000 rpm for 10 minutes, and the pellet was resuspended in 4 ml of SM solution. The bacteriophage of $9.0×10^8$ PFU (plaque forming unit) was inoculated thereto (MOI: multiplicity of infection=0.001), and left at 37° C. for 20 minutes. The solution was inoculated into 150 ml of LB media, and cultured at 37° C. for 5 hours. Chloroform was added to a final volume of 1%, and the culture solution was shaken for 20 minutes. DNase I and RNase A were added to a final concentration of 1 μg/ml, respectively. The solution was left at 37° C. for 30 minutes. NaCl and PEG (polyethylene glycol) were added to a final concentration of 1 M and 10% (w/v), respectively and left at 4° C. for an additional 3 hours. The solution was centrifuged at 4° C. and 12,000 rpm for 20 minutes to discard the supernatant. The pellet was resuspended in 5 mL of SM solution, and left at room temperature for 20 minutes. 4 mL of chloroform was added thereto and mixed well, followed by centrifugation at 4° C. and 4000 rpm for 20 minutes. The supernatant was filtered using a 0.2 μm filter, and the bacteriophage was purified by glycerol density gradient ultracentrifugation (density: 40%, 5% glycerol at 35,000 rpm and 4° C. for 1 hour). The purified bacteriophage was designated as "Bacteriophage ΦCJ11", and resuspended in 300 μl of SM solution, followed by titration. The bacteriophage ΦCJ11 was deposited at the Korean Culture Center of Microorganisms (361-221, Honje 1, Seodaemun, Seoul) on Sep. 9, 2011 under accession number KCCM11208P.

Example 2: Examination on ΦCJ11 Infection of *Salmonella*

To analyze the selected bacteriophage for lytic activity on *Salmonella* species other than SC, attempts were made of cross infection with other *Salmonella* species. As a result, ΦCJ11 infected SC (*Salmonella choleraesuis*), ST (*Salmonella typhimurium*), SD (*Salmonella derby*), SN (*Salmonella newport*), SI (*Salmonella infantis*), SA (*Salmonella arizonae*) and SB (*Salmonella bongori*), but did not infect SE (*Salmonella enteritidis*), SG (*Salmonella gallinarum*), and SP (*Salmonella pullorum*) (Table 1 and FIG. 2).

TABLE 1

| ΦCJ11 Infection of *Salmonella* | | |
|---|---|---|
| Serotype | Strain name | Phage plaque formation |
| SC | ATCC 10708 | ◯ |
| SN | SL 317 | ◯ |
| SD | ATCC 2468 | ◯ |
| SE | SGSC 2282 | X |
| SG | SGSC 2293 | X |
| SA | ATCC 12398 | ◯ |
| SB | ATCC 12397 | ◯ |
| ST | 13 | ◯ |
| SI | SARB 26 | ◯ |
| SP | SGSC 2295 | X |

\* ATCC: American Type Culture Collection
\* SGSC: *Salmonella* Genetic Stock Center Moreover, FIG. 2 is a photograph showing the formation of ΦCJ11 plaques in a lawn of *salmonella* bacteria. As shown in FIG. 2 (A,B; SC, C; SG, D; ST, E; SI, F,G; SD, H; SN), plaque formation was observed in lawns of SC, ST, SI, SD and SN, but not in lawns of SG.

Example 3: Morphology of ΦCJ11

The purified ΦCJ11 was diluted in the SM buffer solution, and then mounted on a copper grid, stained with 2% uranyl acetate for 3 to 5 seconds, and dried. Examination under a transmission electron microscope (LIBRA 120, Carl Zeiss transmission electron Microscope, 80 kV, magnification of ×120,000×200,000) was performed (FIG. 1). FIG. 1 is an electron microscopy photograph of ΦCJ11. As shown in FIG. 1, it was found that the purified ΦCJ11 belongs to the family Siphoviridae of morphotype B1, characterized by an isometric capsid and a long non-contractile tail.

Example 4: Protein Pattern Analysis of ΦCJ11

15 μL of a ΦCJ11 solution purified at a titer of $10^{11}$ PFU/mL was mixed with 3 μL of a 5×SDS sample solution, and heated for 5 minutes. 12% SDS-PAGE was performed, and then the gel was stained with Coomassie blue for 1 hour at room temperature (FIG. 3). FIG. 3 is the result of SDS-PAGE of the isolated bacteriophage ΦCJ11, in which Precision plus protein standard (BIO-RAD) was used as a marker. As shown in FIG. 3, the major proteins were detected at 33 kDa, 55 kDa and 69.5 kDa.

Example 5: Analysis of Total Genomic DNA Size of ΦCJ11

Genomic DNA of the purified ΦCJ11 was isolated using ultracentrifugation. In detail, to the purified ΦCJ11 culture medium were added EDTA (ethylenediaminetetraacetic acid (pH 8.0)), proteinase K, and SDS (sodium dodecyl sulfate) at a final concentration of 20 mM, 50 ug/mL, and 0.5% (w/v), respectively, followed by incubation at 50° C. for 1 hour. An equal volume of phenol (pH 8.0) was added and mixed well. After centrifugation at room temperature and 12,000 rpm for 10 minutes, the supernatant was mixed well with an equal volume of PC (phenol:chloroform=1:1). Another centrifugation was performed at room temperature and 12,000 rpm for 10 minutes. Then, a supernatant was obtained, and mixed with an equal volume of chloroform, followed by centrifugation at room temperature and 12,000 rpm for 10 minutes. The obtained supernatant was mixed with 1/10 volume of 3 M sodium acetate and two volumes of cold 95% ethanol, and left at −20° C. for 1 hour. After centrifugation at 0° C. and 12,000 rpm for 10 minutes, the supernatant was completely removed, and the DNA pellet was dissolved in 50 μL of TE (Tris-EDTA (pH 8.0)). The extracted DNA was diluted 10-fold, and measured for absorbance at $OD_{260}$ to determine its concentration. 1 μg of the total genomic DNA was loaded onto 1' PFGE (pulse-field gel electrophoresis) agarose gel, and electrophoresed at 14° C. for 22 hours in a BIORAD CHEF DR II PFGE system under the conditions of switch time ramp for 50-90 seconds, 6 V/cm (200V). The CHEF DNA Size Standard Lambda Ladder (Bio-Rad) was used as a DNA size marker (FIG. 4). FIG. 4 is the result of PFGE of the isolated bacteriophage ΦCJ11. As shown in FIG. 4, DNA of approximately 140 kbp present between 48.5 to 1,000 kbp was observed.

Example 6: Genetic Analysis of ΦCJ11

For the genetic analysis of the purified ΦCJ11, 5 μg of the genomic DNA of ΦCJ11 was double digested with the restriction enzymes PstI, XbaI and BamHI, EcoRI and SalI. The vector pCL1920 (Promega) was digested with the restriction enzymes PstI, XbaI and BamHI, EcoRI and SalI, and then treated with CIP (calf intestinal alkaline phosphatase). The digested genomic DNA was mixed at a ratio of 3:1 with the vector, and ligated at 16° C. for 2 hours. The resulting recombinant vector was transformed into *E. coli* DH5a which was then plated on an LB plate containing specinomycin and X-gal (5-bromo-4-chloro-3-indolyl-beta-D-galactopyranoside) for selection of blue/white colonies. The selected colonies were cultured for 16 hours in a culture medium containing the antibiotic with shaking. Then, plasmids were extracted using a Plasmid purification kit (Promega).

The cloning of the plasmids was confirmed by PCR using primer sets of FTR135 and FTR136 (SEQ ID NOs. 13 and 14) and selection was made only of insert fragments having a size of 1 kb or longer. Their nucleotide sequences were analyzed using the primer sets. The nucleotide sequences thus obtained were given in SEQ ID NOs. 1 to 4, respectively, each having a size of 1 to 2 kbp or less, and analyzed for sequence similarity with the aid of NCBI blastx and blastn program, and the results are summarized in Table 2, below.

TABLE 2

Comparison of Sequence Similarity between ΦCJ11 and Other Bacteriophages

| | Organism | Protein | Blastx | | | |
| --- | --- | --- | --- | --- | --- | --- |
| | | | Query | Subject | Identity | e-value |
| 1 | Enterobacteria phage T5 | hypothetical protein | 436-627 | 1-64 | 63/64 (98%) | 7e−32 |
| | Enterobacteria phage SPC35 | hypothetical protein | 10-423 | 1-139 | 127/139 (91%) | 3e−31 |
| | Enterobacteria phage SPC35 | hypothetical protein | 3-863 | 30-315 | 264/291 (91%) | 2e−116 |
| | Enterobacteria phage T5 | hypothetical protein | 3-863 | 30-315 | 255/291 (88%) | 1e−113 |
| | Enterobacteria phage EPS7 | hypothetical protein | 3-761 | 29-281 | 235/253 (93%) | 7e−107 |
| | *Klebsiella* phage KP15 | hypothetical protein | 9-761 | 22-276 | 217/255 (85%) | 4e−100 |
| | Enterobacteria phage RB43 | putative SPFH domain-containing protein | 9-839 | 18-257 | 223/281 (79%) | 7e−99 |

TABLE 2-continued

Comparison of Sequence Similarity between ΦCJ11 and Other Bacteriophages

| | Organism | Protein | Blastx Query | Subject | Identity | e-value |
|---|---|---|---|---|---|---|
| | Enterobacteria phage RB16 | hypothetical protein | 9-761 | 18-272 | 219/255 (86%) | 2e-98 |
| 2 | Enterobacteria phage EPS7 | hypothetical protein | 412-771 | 1-120 | 109/120 (91%) | 7e-57 |
| | Enterobacteria phage T5 | hypothetical protein | 490-771 | 1-94 | 94/94 (100%) | 3e-46 |
| | Enterobacteria phage T5 | D11 protein | 532-2 | 1-177 | 175/177 (99%) | 5e-96 |
| | Enterobacteria phage SPC35 | D11 protein | 532-2 | 1-177 | 174/177 (98%) | 2e-95 |
| | Enterobacteria phage EPS7 | D11 protein | 532-8 | 1-175 | 163/175 (93%) | 4e-90 |
| | Enterobacteria phage EPS7 | hypothetical protein | 872-528 | 5-120 | 96/116 (83%) | 2e-46 |
| 3 | Enterobacteria phage SPC35 | tail protein Pb4 | 777-4 | 1-258 | 221/258 (86%) | 4e-128 |
| | Enterobacteria phage T5 | tail protein Pb4 | 777-4 | 1-258 | 197/258 (76%) | 6e-115 |
| | Enterobacteria phage SPC35 | tail protein Pb3 | 1322-780 | 769-949 | 178/181 (98%) | 2e-96 |
| | Enterobacteria phage EPS7 | tail protein Pb3 | 1322-780 | 769-949 | 160/181 (88%) | 9e-88 |
| | Enterobacteria phage T5 | structural tail protein Pb3 | 1322-780 | 769-949 | 156/181 (86%) | 8e-84 |
| | Enterobacteria phage EPS7 | tail protein Pb4 | 423-4 | 1-140 | 112/140 (80%) | 2e-62 |
| 4 | Enterobacteria phage SPC35 | flap endonuclease | 980-564 | 153-291 | 138/139 (99%) | 1e-73 |
| | Enterobacteria phage T5 | flap endonuclease | 980-564 | 153-291 | 138/139 (99%) | 1e-73 |
| | Enterobacteria phage EPS7 | flap endonuclease | 980-564 | 153-291 | 135/139 (97%) | 4e-72 |
| | Enterobacteria phage SPC35 | putative deoxyUTP pyrophosphatase | 564-157 | 1-136 | 130/136 (96%) | 3e-70 |
| | Enterobacteria phage T5 | putative deoxyUTP pyrophosphatase | 564-160 | 1-135 | 130/135 (96%) | 2e-69 |
| | Enterobacteria phage EPS7 | putative deoxyUTP pyrophosphatase | 564-157 | 1-136 | 128/136 (94%) | 2e-67 |

Example 7: Design of ΦCJ11-Specific Primer Sequences

In order to identify ΦCJ11, ΦCJ11-specific primers were designed on the basis of SEQ ID NOS. 1 to 4. PCR was performed using each primer set of SEQ ID NOS. 5 and 6, SEQ ID NOs. 7 and 8, SEQ ID NOs. 9 and 10, and SEQ ID NOs. 11 and 12. 0.1 μg of the genomic DNA of bacteriophage and 0.5 pmol of each primer were added to a pre-mix (Bioneer), and the final volume was adjusted to 20 μL. PCR was performed with 30 cycles of denaturation; 94° C. 30 seconds, annealing; 55° C. 30 seconds, and polymerization; 72° C., 1.5 minutes (FIG. 5). FIG. 5 is the result of PCR, performed using each primer set for the ΦCJ11 genomic DNA. A; a primer set of SEQ ID NOs. 5 and 6, B; a primer set of SEQ ID NOs. 7 and 8, C; a primer set of SEQ ID NOs. 9 and 10, and D; a primer set of SEQ ID NOs. 11 and 12. All of A, B, C and D lanes had PCR products of approximately 1 to 2 kbp. As shown in FIG. 5, the PCR products thus obtained had a size of approximately 1 kbp or more to 2 kbp or less, with the primer sets of SEQ ID NOs. 5 and 6, SEQ ID NOs. 7 and 8, SEQ ID NOs. 9 and 10, and SEQ ID NOs. 11 and 12.

Example 8: pH Stability of Bacteriophage

In order to determine whether ΦCJ11 survives with stability under the low pH environment in the stomach of pig, ΦCJ11 was assayed for stability in a wide range of pH (pH 2.1, 2.5, 3.0, 3.5, 4.0, 5.5, 6.4, 6.9, 7.4, 8.2, 9.0, 9.8 and 11.0). Various pH solutions (sodium acetate buffer (pH 2.1, pH 4.0, pH 5.5, and pH 6.4), sodium citrate buffer (pH 2.5, pH 3.0, and pH 3.5), sodium phosphate buffer (pH 6.9 and pH 7.4) and Tris-HCl (pH 8.2, pH 9.0, pH 9.8 and pH 11.0)) were prepared to have a concentration of 0.2 M. 180 μL of each pH solution was mixed with 20 μL of a bacteriophage solution ($1.0 \times 10^{11}$ PFU/mL) to give each pH solution a concentration of 1 M, followed by incubation at room temperature for 2 hours. The reaction solution was serially diluted, and 10 μL of each dilution was cultured at 37° C. for 18 hours by a soft agar overlay method to determine the titers of the phage lysates (FIG. 6). FIG. 6 is the result of acid-resistance assay on the bacteriophage ΦCJ11, showing the number of surviving bacteriophage at pH 2.1, 2.5, 3.0, 3.5, 4.0, 5.5, 6.4, 6.9, 7.4, 8.0, 9.0, 9.8 and 11.0. The bacteriophage ΦCJ11 did not lose its activity until pH 5.5. However, the bacteriophage ΦCJ11 showed reduced activity at pH 4 and pH 3.5, and completely lost its activity at pH 3.0 or lower, as compared to a control. As shown in FIG. 6, the bacteriophage did not lose its activity and remained stable down to pH 5.5 whereas it lost its activity at pH 3.0 or lower.

Example 9: Heat Stability of Bacteriophage

For use as a feed additive, the bacteriophage was assayed for stability to the heat generated during a formulation process. In this regard, 200 μL of a ΦCJ11 solution with a titer of $1.0 \times 10^{11}$ PFU/mL was incubated at 37° C., 45° C., 53° C., 60° C., and 70° C. for 0 minute, 10 minutes, 30 minutes, 60 minutes and 120 minutes. The solution was serially diluted, and 10 μL of each dilution was cultured at 37° C. for 18 hours by a soft agar overlay method to determine the titers of phage lysates (FIG. 7). FIG. 7 is the result of heat-resistance assay on the bacteriophage ΦCJ11, showing the number of surviving bacteriophage at 37° C., 45° C., 53° C., 60° C., and 70° C. for 0, 10, 30, 60 and 120 minutes. As shown in FIG. 7, the bacteriophage ΦCJ11 maintained its activity even though exposed at 60° C. up to 2 hours.

Example 10: Desiccation Tolerance of Bacteriophage

For use as a feed additive, the bacteriophage ΦCJ11 was assayed for tolerance to the dry condition set for a formulation process. On the basis of the results obtained from the heat stability assay, a desiccation assay was performed using a SpeedVac concentrator. 200 μL of a ΦCJ11 solution having a titer of $1.0 \times 10^{11}$ PFU/mL was dried under vacuum at 60° C. for 2 hours, and the pellet thus obtained was completely re-suspended in 200 μL of the SM solution at 4° C. for one day, and measured for titer values (FIG. 8). FIG. 8 is the result of desiccation tolerance assay on the bacteriophage ΦCJ11 dried with the aid of a SpeedVac concentrator. As shown in FIG. 8, when titer changes under the dry condition were measured in comparison with pre-drying titers, the activity was maintained at 60° C. up to 1 hour.

Example 11: Infection Spectrum of Bacteriophage

ΦCJ11 was assayed for lytic activity against the wild-type (2 strains), *Salmonella choleraesuis* (5 strains), *Salmonella typhimurium* (17 strains), *Salmonella infantis* (4 strains), *Salmonella newport* (6 strains), *Salmonella* derby (2 strains) and *Salmonella dublin* (3 strains), obtained from Laboratory of Avian Diseases, College of Veterinary Medicine, Seoul National University, in addition to SC (ATCC SC10708) used in the experiment. 150 μL of each strain shaking culture medium ($OD_{600}=2$) was mixed, and 10 μL of ΦCJ11 solution having a titer of 10'PFU/mL was cultured at 37° C. for 18 hours using a soft agar overlay method to monitor the formation of plaques (Table 3). Formation of phage plaque was observed in 8 strains of SC.

TABLE 3

| Serotype | Strain name | | Phage plaque formation | serotype | Strain name | | Phage plaque formation |
|---|---|---|---|---|---|---|---|
| SC | *S. choleraesuis* | ATCC 2929 | o | SI | *S. infantis* | SARB 26 | o |
| | *S. choleraesuis* | ATCC 2930 | o | | *S. infantis* | SARB 27 | o |
| | *S. choleraesuis* | ATCC 2932 | o | | *S. infantis* | S1326/28 | o |
| | *S. choleraesuis* | ATCC 2933 | o | | *S. infantis* | B09-106 | o |
| | *S. choleraesuis* | ATCC 2425 | o | SN | *S. newport* | SARB 36 | o |
| | *S. choleraesuis* | ATCC 10708 | o | | *S. newport* | SARB 37 | o |
| | *S. choleraesuis* | SNU#1 | o | | *S. newport* | SARB 38 | o |
| | *S. choleraesuis* | SNU#2 | o | | *S. newport* | 7257 | o |
| ST | *S. typhimurium* | SNU ST1 | o | | *S. newport* | SL 317 | o |
| | *S. typhimurium* | SNU ST2 | o | | *S. newport* | SL 254 | o |
| | *S. typhimurium* | SNU ST4 | o | SD | *S. derby* | ATCC 2466 | o |
| | *S. typhimurium* | SNU ST7 | o | | *S. derby* | ATCC 2468 | o |
| | *S. typhimurium* | SNU ST8 | o | SD | *S. dublin* | SA 4405 | o |
| | *S. typhimurium* | SNU ST11 | o | | *S. dublin* | RKS 4699 | o |
| | *S. typhimurium* | SNU ST12 | o | | *S. dublin* | 88/6 | o |
| | *S. typhimurium* | SNU ST13 | o | SA | *S. arizonae* | ATCC 12398 | o |
| | *S. typhimurium* | SNU ST14 | o | SB | *S. bongori* | ATCC 12397 | o |
| | *S. typhimurium* | SNU ST17 | o | SH | *S. heidelberg* | SARA 33 | o |
| | *S. typhimurium* | SNU ST18 | o | | *S. heidelberg* | SARA 23 | o |
| | *S. typhimurium* | SNU ST19 | o | SM | *S. maimi* | SARB 28 | o |
| | *S. typhimurium* | SNU ST20 | o | | *S. maimi* | SARB 29 | o |
| | *S. typhimurium* | SNU ST26 | o | SP | *S. panama* | SARB 39 | o |

TABLE 3-continued

| Wild-type strains SC, ST, SD, SI, SN infected by ΦCJ11 | | | | | |
|---|---|---|---|---|---|
| Serotype | Strain name | Phage plaque formation | serotype | Strain name | Phage plaque formation |
| S. typhimurium | SNU ST38 | ○ | S. panama | SARB 40 | ○ |
| S. typhimurium | SNU ST41 | ○ | S. panama | SARB 41 | ○ |
| S. typhimurium | SNU ST42 | ○ | S. panama | 7261 | ○ |

SGSC: *Salmonella* genetic stock center
ATCC: American Type Culture Collection
SNU: Laboratory of Avian Diseases, College of Veterinary Medicine, Seoul National University Example 12: Toxicity Assay of Bacteriophage Dermal and ocular irritation tests were performed in specific-pathogen-free (SPF) New Zealand white rabbits, which are commonly used in the toxicity test of bacteriophage ΦCJ11 for the prevention of *salmonellosis* and *salmonella* food poisoning, and of which experimental data were accumulated to allow easy analysis of experiment results. The normal abdominal skin (non-injured skin) and injured abdominal skin of rabbits were covered and contacted with 2.5 cm×2.5 cm of gauze applied with the test substance, and each 0.5 mL/site was applied. No changes in general symptoms were observed, and a slight weight loss was observed 1 day after application of the test substance, which can likely to be attributed to stress due to occlusive application of the test substance. In the dermal irritation test, the primary irritation index (PII) was 0.33, indicating no irritant. For the ocular irritation test, the left eye of a rabbit was applied with the test substance, and then compared to the right eye, which was not applied with the test substance. During the experimental period, general symptoms and abnormal changes in body weight related to application of the test substance were not observed. After application of the test substance, the eye examination showed that the index of acute ocular irritation (IAOI) was "0", indicating no irritant. Therefore, these results indicate that the novel bacteriophage ΦCJ11 has no toxicity.

Further, toxicity assay was performed by single oral administration of Sprague-Dawley rats with ΦCJ11. A test substance-administered group treated with $1 \times 10^{11}$ PFU/kg of ΦCJ11 and an excipient control group treated with a vehicle [20 mM Tris-HCl (pH 7.0)+2 mM $MgCl_2$] as an excipient were prepared, and 10 rats of each group (5 each of female and male sexes) were orally administered with a single dosage. Mortality, general symptoms, changes in body weight, and autopsy findings were monitored for 2 weeks and compared to each other. Monitoring was conducted every 6 hours, starting from 30 minutes to 1 hour after administration on the day of administration. Then, general symptoms were monitored once a day for 14 days, and recorded thereof (Tables 4 and 5).

TABLE 4

Mortality and general symptoms after oral administration of ΦCJ11

| | Done | Day after treatment | | | | | | | | | | | | | |
|---|---|---|---|---|---|---|---|---|---|---|---|---|---|---|---|
| Sex | (pfu) | 1 | 2 | 3 | 4 | 5 | 6 | 7 | 8 | 9 | 10 | 11 | 12 | 13 | 14 | Mortality |
| Male | Control | 0 | 0 | 0 | 0 | 0 | 0 | 0 | 0 | 0 | 0 | 0 | 0 | 0 | 0 | 0 |
|  | $10^{11}$ | 0 | 0 | 0 | 0 | 0 | 0 | 0 | 0 | 0 | 0 | 0 | 0 | 0 | 0 | 0 |
| Female | Control | 0 | 0 | 0 | 0 | 0 | 0 | 0 | 0 | 0 | 0 | 0 | 0 | 0 | 0 | 0 |
|  | $10^{11}$ | 0 | 0 | 0 | 0 | 0 | 0 | 0 | 0 | 0 | 0 | 0 | 0 | 0 | 0 | 0 |

TABLE 5

Autopsy findings after oral administration of ΦCJ11

| Sex | Done (PFU) | gross finding | Frequency[A] |
|---|---|---|---|
| Male | Control | No gross finding | 5/5 |
|  | $10^{11}$ | No gross finding | 5/5 |
| Female | Control | No gross finding | 5/5 |
|  | $10^{11}$ | No gross finding | 5/5 |

[A]Number of animal with the sign/number of animals examined.

As shown in Tables 4 and 5, none of them died, and neither toxic symptoms nor noticeable clinical symptoms were generated by ΦCJ11. The results are summarized in Tables 4 and 5. Body weights were recorded before administration and 1, 3, 7, 10 and 14 days after administration. No significant changes were observed in body weight compared to the control group.

Meanwhile, the results of body weight changes indicate that ΦCJ11 does not cause a toxic reaction sufficient to reduce appetite or to change body weight. These results are shown in FIG. 9. FIG. 9 is the results of body weight changes due to toxicity after single oral administration of Sprague-Dawley rats with ΦCJ11. As shown in FIG. 9, observation of body weight changes before administration and 1, 3, 7, 10 and 14 days after administration with ΦCJ11 showed that no significant changes in body weight were found in comparison with the control group (■; male control, □; ΦCJ11 male, ●; female control, ○; ΦCJ11 female).

Therefore, it was found that ADL of the novel bacteriophage ΦCJ11 exceeds $1 \times 10^{11}$ PFU/kg in both female and male rats, and thus it is non-toxic.

The invention claimed is:

1. A method of preparing an animal feed composition, the method comprising:
   providing a bacteriophage composition comprising bacteriophage as an active ingredient and a additive; and
   mixing the composition with an animal feed base to provide the animal feed composition,
   wherein the bacteriophage has nucleic acid sequences of SEQ ID NOs: 1 to 4.

2. The method of preparing an animal feed composition according to claim 1, wherein the bacteriophage is bacteriophage ΦCJ11 deposited under accession number KCCM11208P.

3. The method of preparing an animal feed composition according to claim 1, wherein the bacteriophage composition further comprises other non-pathogenic microorganisms.

4. The method of preparing an animal feed composition according to claim 3, wherein the other non-pathogenic microorganisms are selected from the group consisting of *Bacillus subtilis, Lactobacillus* sp. strain, filamentous fungi, and yeast including *Saccharomyces cerevisiae*.

5. The method of claim 1, wherein the bacteriophage is in an amount of 0.05 to 10 by dry weight based on 100 parts by dry weight of the feed composition.

6. A method of feeding an animal feed composition to an animal, the method comprising:
   preparing the animal feed composition according to the method of claim 1; and
   feeding the animal feed composition as a feed to the animal.

7. A method of preparing a drinking water composition, the method comprising:
   providing a bacteriophage composition comprising bacteriophage as an active ingredient and a additive; and
   mixing the composition with drinking water to provide the drinking water composition,
   wherein the bacteriophage has nucleic acid sequences of SEQ ID NOs: 1 to 4.

8. The method of preparing a drinking water composition according to claim 7, wherein the bacteriophage is bacteriophage ΦCJ11 deposited under accession number KCCM11208P.

9. The method of preparing a drinking water composition according to claim 7, wherein the bacteriophage composition further comprises other non-pathogenic microorganisms.

10. The method of preparing a drinking water composition according to claim 9, wherein the other non-pathogenic microorganisms are selected from the group consisting of *Bacillus subtilis, Lactobacillus* sp. strain, filamentous fungi, and yeast including *Saccharomyces cerevisiae*.

11. The method of claim 7, wherein the bacteriophage is in an amount of 0.0001 to 0.01 by dry weight based on 100 parts by dry weight of the drinking water.

12. A method of feeding a drinking water composition to an animal, the method comprising:
    preparing the drinking water composition according to the method of claim 7; and
    feeding the drinking water composition as a feed to the animal.

* * * * *

SEQUENCE LISTING

<160> NUMBER OF SEQ ID NOS: 14

<210> SEQ ID NO 1
<211> LENGTH: 1643
<212> TYPE: DNA
<213> ORGANISM: bacteriophage CJ11

<400> SEQUENCE: 1

```
taaactgccg gcttaatatt aaggggagga gcccattatg agtaaatatg gttttgtaaa      60
taacggactt aatcaaagta tgggctccca gcagcccatg ccgggtctgg ataacccta     120
cttacaacag ttgcaacagc gtttagcaga agcgcaacag atgcagcaac aactccagca    180
aaatcctgga agtgttagtc ctatgcaaat gatgcagcaa atgaatgggc agtcgcaaat    240
gccccaacaa atgcagcaac agatgccgca gcagcaagtt cagcaacaaa cccaacaacc    300
gcaggtttct gcggaaggac aggcagtact agccctttc gaagacttcg caaagacaga    360
ggatgggaag cagcttgtat cacttatggg taagtttaat agcttctgcc aaagccaagt    420
tgcaaaagct caaaatggtg gtaataactc ctaaggagga attatgtgtt gcagaaaatc    480
tgtttcgtgc tgcccaatgc ctgtagcacg ttgttgctct tcagcaatgt ttacacaaat    540
accggcgttc aatccgtttg cctttaagcc tactcttatc ctgcccccta gagtagattt    600
tcagtcaagg ttggcctccc gtatgggtgg ttgctgtaat aagagtatat ggttctaaag    660
aaccaaacaa taaagcccct agtcgaaaga cttagggggct tttcttttat cttaaataca    720
gaaaagccct gcgctctcca gggaacgcag ggcttacttc agatgttacg tgcggatatt    780
atttattacg catatccatg atcatttggc catcatagcc agtgccaacc acagtctgcg    840
gtacaccacc tttggtattt ctgagcacga atcatttcaa cttccagtt gcttccagcg    900
aatcatctca ggagtaatgg tacgttgcaa tgcggcgtta gcttcagctt ctttcttagc    960
tgcgtacagt ttggcatctg cgtcacgttc gttagcaata gcttggttat tacgagcttc    1020
gcgatctgct tctgcttgtt taaccttctg ctgtgcttct tgttcaacac gagccagttc    1080
agctttcgca gcattaacct gttcttcacg aactttggta ttctgtacct gttccatgat    1140
taccggtggc aaagtaatat cctgaagaaa tacctgctta actgtgtaac catatgggcg    1200
tgcatactct tcaacttcct gttgaattgc agtttgcaat tgagcctgaa ttttagcatc    1260
aaacaaatct tgtgctttag gtacagactt accaaactca cgaatagtag acagtaattt    1320
ttcagttaca tatttgtcta acgcttgatc ctgagtacct gcattaatac ggttaatcgg    1380
tgccttagaa ccatcaaact gcaacataac agtcaggtca acagtggatt taaacttatc    1440
ctgactagga acctgaagtt tatctaattt tagagcaata tctttagtac taaaagtatc    1500
gaaagaagca aaaggattta caatatgaaa gccgggtaat actgggctag ggtcaacttt    1560
acccaggaaa gtctgggttt taacagtacc gtcttgaaca acagtatagg agttaagggc    1620
cagaactaaa cctaccaaac caa                                            1643
```

<210> SEQ ID NO 2
<211> LENGTH: 1464
<212> TYPE: DNA
<213> ORGANISM: bacteriophage CJ11

<400> SEQUENCE: 2

| | |
|---|---|
| taggtataca ctgggatact aactcttcta aatggaaggt agaaataact aactgtatag | 60 |
| gtgttaaaat atatggtggg ttattcccctt atgaagaatt agagttagct ataaataaag | 120 |
| ctaacgaact tagagcacag catctaggta tggattccag gcaagaacta ttcaaaggat | 180 |
| atatttgccg acgtgaggac ttagataagt aaaattgcat ttggcaatag ctcataaatg | 240 |
| atgtataata tatacataaa tttgagagag aaagtttcgg attgataaga aagtccgaag | 300 |
| cagaaaaata aaaattttag ttgctaaatt ctctcgaaat ctagtataat atatacataa | 360 |
| attcgaggag aaaacaaaaa ttaaattctt cgattatgaa aagctatact tactagctag | 420 |
| aggaaattcc gacctaatta ttaagttatt caaaagaatg cttacagagc ctgatgctca | 480 |
| ccaattattg gtcggttcct cattcattt gaatgaatca acaatagttg ataatccaaa | 540 |
| taaattgtct aatagacaac tggcagaata tctaggaatt ttaagtctac gaaattatgc | 600 |
| cgaatacaag tttacaaacg atcctagttt ggacatacaa tatgttccag tatggatacc | 660 |
| acgtttagta atcgacacta acccactaat cgcaattaac aaatcgaaat taatctttaa | 720 |
| agaggaaata aaatatggct aagtcttggg gcgaaactac tggcggttct aacgataaaa | 780 |
| tcgaattcct gaagttcaac aacggtatca ctcgtgttcg tatcgtttct ggtgttcttc | 840 |
| cacgttatgt ctattggctg actaataaag agggtagcgt agctcctttc gaatgtctcc | 900 |
| gttttaaccg tgacaaagag agctttgttc gtggtaaagc tgatccggtt catgagatgg | 960 |
| gcttcttcga gaaagaactg gataaagatg gtaatcgtgt tccgctgaaa ccgaagaaaa | 1020 |
| actatatcgc ttttgttatc gaccgttctg ataacaaact gaaagtaatg gaagtcaagg | 1080 |
| ctactattct gaaaggcatc cagtctatca tgaagcagtt gagtctggca actccgtttg | 1140 |
| atattgatat ttctatcgag aaaaaaggta aggtttcga tactgagtat gatgtacagc | 1200 |
| agattgctgc tatgcagttc cagattaagc tgcaagatcc taacagtgca gagtctaagc | 1260 |
| aatatgctgc aggcatgcaa gcttggcgta atcatggtca tagctgtttc ctgtgtgaaa | 1320 |
| ttgttatccg ctcacaattc cacacaacat acgagccgga agcataaagt gtaaagcctg | 1380 |
| gggtgcctaa tgagtgagct aactcacatt aattgcgttg cgctcactgc ccgctttcca | 1440 |
| gtcgggaaac ctgtcgtgcc agct | 1464 |

<210> SEQ ID NO 3
<211> LENGTH: 1324
<212> TYPE: DNA
<213> ORGANISM: bacteriophage CJ11

<400> SEQUENCE: 3

| | |
|---|---|
| tactgaatct atataagaaa caacaaattc gcgaacgtta gcgccagctc ctctatccca | 60 |
| ttcccattgt acacggagat catatctttc tttaccatca gcaatccttg cagctttgaa | 120 |
| agtaatgttg ttaggagcag taggaggtac aaagttatac tctacagtaa gaactttgga | 180 |
| aaattcaaag tatccagaag agtctacagt tacaccatct ggcatggtaa cttgcccaga | 240 |
| tatgcgtact ttgtaatccc caacaggaac accaccaaat ctaatagtgg gagatagtgg | 300 |
| acctatataa tactttaccc acgggctatt tgaaggttga gtacttttta actcaatagt | 360 |
| acaataacta gcttctcctg tagtctctat aactactata ggggcaccta cacccacatc | 420 |
| tactggatca gcctctgatc tagcggcagt aatagtaggt tttctcttag tactaaaggt | 480 |
| agttttattg gataagttta tgccaatttt agcctctaat agctcagagt ctataataga | 540 |
| gtcatagaaa gccccttgaa cctcataaga agttgaaggg gttagattat taatcattac | 600 |
| aaagaaagta tctataccgg tatagtcacg tctatcaata cttcctccta actttaacca | 660 |

| | | |
|---|---|---|
| aaaggatcta ccaataacgt cataatcagt atatatagag tgctggacat atgccattgt | 720 |
| atatccagtc attatactat ttaagaccat tttggctggt gcattattcg aaatcattaa | 780 |
| atggatgccc actccacaga ctgttcccca tcatctcctt ctgctctaat acgaaaatat | 840 |
| agttttctat tgatccctag agcatcactg ttatggagag caaaatctgc cttattatac | 900 |
| attaataaat agtcataagt atactgattt tcaatacgta cacttcttag cattctattc | 960 |
| tgggaatcat agatctccag agtatagaat atactttcta ttatatcttc ttctggtatc | 1020 |
| ctatcccaag ctagttttac gtctgggccg acaaactcag ttacatctcc agaagccgta | 1080 |
| ttagttaccc taaaattaga tactacgctt aggttttttag cagagttaag ttctatagat | 1140 |
| aatgttactg agaacttct tctaccgttt atatccacag cccttatttc aaatattgct | 1200 |
| aaacctgcag gttctccaac tatctcttgg atcatgcgtt cattgggatt tgtttctagt | 1260 |
| tgctgcacaa tatacggctc agcatggcct gaatgtacga tagaatagta aactacgtta | 1320 |
| ttag | 1324 |

<210> SEQ ID NO 4
<211> LENGTH: 1666
<212> TYPE: DNA
<213> ORGANISM: bacteriophage CJ11

<400> SEQUENCE: 4

| | | |
|---|---|---|
| cagaaaataa cattaccttc tttatctgtt tttagtacaa ccgtttctgg tttagtagtt | 60 |
| ttaatctgat aagttgatgt actagtatca atacctacca tattaggatc ggtaaaatta | 120 |
| tttgcttcct gaacttccaa atccgccttc cccacgatct gtctcccta gttcgtcaac | 180 |
| gatttcaaaa ttatgagttg agtagtgtgg tactactact agctgacaaa gtctttcaaa | 240 |
| attttccaga gtttgaattt cagaaccata gttataaagg ttcatcttaa tagttccacg | 300 |
| atagtctgag tcaatcactc ctgcggtgtt tgcaatcatc agatgacgct tacctaagga | 360 |
| gctacgagga actaccaaac cgaaccaacc tcgcggaatt tctaccgcga caccggtgtc | 420 |
| aatcattaag gatttgcctg gtgcaatagc acgtaaatct gcagcagggt tagtaccaaa | 480 |
| gaacgctcgc agatccatac ctgcggcatc ttcggaacca atcttaggcg tacaatctgg | 540 |
| atgagttaat ttaattttaa tcattgttct gcaatctcca aaatatcttt tgtaaattta | 600 |
| tctaatacat cttgacctac agcagcaata gcatccacac agtaggtagg taaatcaacc | 660 |
| agaattaggt ttcgataaag caattcttcc gaagcattta aattctgtat atatttctgt | 720 |
| tttccaggca gtggaagctg atcaataata tccagaacgt taccaaattc acgaataata | 780 |
| ttatacccac gctttgcccc aatacctca cacctcgga tattatcccc taaatcaccc | 840 |
| ataattgctt tcagggagat aaactgctct acatcgtcaa cattatgatg ctcatacata | 900 |
| tcacgaagat gatattcacg acgtgttgtg aaagagaagc gagatacttt atcagttaat | 960 |
| aaagtatccc agtcaccatc ggtagaaatt agccaaacat gatcatatag atgcccaatc | 1020 |
| agcttaacaa tataagctgc catatcatct gcttctaccc cacgaatagt gaaagttggg | 1080 |
| aatgtagttt cacataattc gaaagcatct ttcaagtact cgaagaattg ttcatctaat | 1140 |
| gctttctcct cttccgtacg ctgcgagtat ttctcatctc gattcccttt atactcaggg | 1200 |
| agatgctcta ggcggaatgc agacttccct ttatctccta aaactattgt agttctagca | 1260 |
| gagtaagatt ttgcaagaga ctgaatagtg gaaacataac ttgaggcaaa tggtttttta | 1320 |
| ctattgttat gcttgaagcg aaagcctaag ttagttccat cgacaatcat taggttacga | 1380 |

```
cgggaagcca tttcggcttc ctcttcctca ataaattttc cccaggattt actcattatt    1440
taattaagtc ctcaacagat gcatgatgta gccacggctc aaataaacca attacgattt    1500
ccatgtcttt cttatttaac accatatggg tacgactcat taagttgtca accatcgggt    1560
ctgagctatc caaagctatt aaccactgtc ctctgtcttt tttgaatatt aatgcaggtt    1620
tggagttcat ctgctcacct tcacgtgagc actgctgcca ccactt                  1666

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cccattatga tgaaataggg                                                 20

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ctatactgtt gttcaagac                                                  19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gatactaact cttctaaatg                                                 20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cttagactct gaactgttag                                                 20

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
ctgaatctat ataagaaaca ac                                              22

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
```

```
cgaagtttac tattctatcg                                             20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gtttttagta caaccgtttc                                             20

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
cagatgaact ccaaacctg                                              19

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
cgggcctctt cgctattacg                                             20

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
aggcttaccc gtcttactgt cg                                          22
```